United States Patent [19]

Sugihara et al.

[11] Patent Number: 4,844,786
[45] Date of Patent: Jul. 4, 1989

[54] MEANS FOR ELECTROPHORESIS

[75] Inventors: Mitsuru Sugihara; Masashi Ogawa, both of Asaka, Japan

[73] Assignee: Fuji Photo Film Co., Ltd., Kanagawa, Japan

[21] Appl. No.: 160,161

[22] Filed: Feb. 25, 1988

[30] Foreign Application Priority Data

Feb. 26, 1987 [JP] Japan .................................. 62-43702
Feb. 26, 1987 [JP] Japan .................................. 62-43703

[51] Int. Cl.$^4$ ............................................ G01N 27/26
[52] U.S. Cl. ............................. 204/299 R; 204/182.8
[58] Field of Search .............. 204/299 R, 182.8, 180.1

[56] References Cited

U.S. PATENT DOCUMENTS 4,576,693 3/1986 Kreisher et al. ............ 204/299 R X

OTHER PUBLICATIONS

Olsson et al., "Uniformly Spaced Banding Pattern in DNA Sequencing Gels by Use of Field-Strength Gradient".

Primary Examiner—John F. Niebling
Assistant Examiner—John S. Starsiak, Jr.
Attorney, Agent, or Firm—Jules E. Goldberg

[57] ABSTRACT

A means for electrophoresis suitably employable for analysis of biopolymers such as proteins, as well as for determination of base sequence of DNA, RNA, their fragments, and their derivatives is disclosed. The means comprises a membrane of an aqueous polyacrylamide gel for electrophoresis which is sandwiched between a plane support and a plane covering sheet. The membrane has a thickness gradient in its electrophoresis direction.

8 Claims, 3 Drawing Sheets

MEANS FOR ELECTROPHORESIS

BACKGROUND OF THE INVENTION

1. Field of the invention

This invention relates to a means for electrophoresis comprising an aqueous polyacrylamide gel which is suitably employable for analysis of biopolymers such as proteins, as well as for determination of base sequence of DNA, RNA, their fragments, and their derivatives, and more particularly relates to an improvement of a membrane (slab or layer) for electrophoresis having an improved molecular sieve function over a wide range, that is, from a low molecular weight portion to a high molecular weight portion.

2. Description of prior art

Recently, electrophoresis has been frequently used for the analysis of biopolymers such as proteins, or for determination of base sequence of DNA or RNA.

As the membrane or sheet for the electrophoresis, a filter paper was previously employed, but recently an agarose gel membrane or a polyacrylamide gel membrane (or medium) has been employed from the viewpoints of their advantageous properties. Particularly, the polyacrylamide gel membrane showing a molecular sieve function and a function to separate, fractionate, analyse or assay a high molecular weight portion of proteins originating from a living body is widely used. More particularly, in the method for determination of base sequence of DNA, RNA, their fragments, and their derivatives according to a post-label method, a procedure of slab electrophoresis using a polyacrylamide gel membrane has become essential.

In the case that the analysis of proteins or determination of base sequence of DNA, RNA, their fragments is performed utilizing difference of their molecular weights in a run of electrophoresis, it is known that a polyacrylamide gel membrane having a uniform thickness gives a wide band interval in a low molecular weight portion and a narrow band interval in a high molecular weight portion. Thus, the separation of proteins, or DNA or RNA is not satisfactory in the high molecular weight portion. Accordingly, a polyacrylamide gel membrane which has an improved molecular sieve function, i.e., up to a high molecular weight portion, is required. A polyacrylamide gel membrane having a polyacrylamide gel concentration gradient or a buffer solution concentration gradient in the direction of electrophoresis is already used to analyze proteins equally over a wide range of molecular weight part. Japanese Patent Provisional Publication No. 60(1985)-235819 (corresponding to European Patent Provisional Publication No. 0159694A) describes a process for the preparation of polyacrylamide gel membrane for electrophoresis having a polyacrylamide concentration (i.e., gel concentration or pore size) gradient (gradient gel membrane) and an apparatus thereof. The polyacrylamide gel membrane can be prepared by closslinking polymerization of an aqueous solution containing an acrylamide and a crosslinking agent in the form of a thin layer formed on a surface of a support using an ionization rays such as an electronic beam to give a concentration gradient in the gel membrane. However, it is extremely complicate to manufacture the apparatus and to control the electronic beam. Further, the gradient gel membrane has problems of its mass scale production such that the preparation thereof requires a long period of time, reproducibility is insufficient, and preparation thereof frequently failed. Furthermore, the gradient gel membrane is apt to deform when it is dyed to visualize the segregated and fractionated image, because the degree of swelling is affected by the polyacrylamide gel concentration.

SUMMARY OF THE INVENTION

An object of the present invention is to provide a means for electrophoresis comprising an aqueous polyacrylamide gel (referred to herein as "gel membrane" or "slab gel") employable for analysis of biopolymers such as proteins, as well as for determination of base sequence of DNA, RNA, their fragments, and their derivatives which is able to give such an improved molecular sieve function that biopolymers or fragments can be equally separated in a wide range from a low molecular weight portion to a high molecular weight portion.

There is provided by the present invention a means for electrophoresis comprising a membrane of an aqueous polyacrylamide gel formed by crosslinking polymerization of an acrylamide compound and a crosslinking agent in the presence of water sandwiched between a support and a covering sheet, wherein said membrane has a thickness gradient (or gradation) in its electrophoresis direction.

The means for electrophoresis of the invention can be employed in a conventional electrophoresis process comprising the steps of applying a sample on the aqueous gel membrane and developing (i.e., subjecting) to electrophoresis the applied sample in the electrophoresis direction on the membrane.

BRIEF DESCRIPTION OF THE DRAWINGS

FIG. 1 shows a V-shaped vertical section of a gel membrane having a maximum thickness (at a start point and an end point in the direction of electrophoresis) of 1.6 mm, a minimum thickness (at the center in the direction of electrophoresis) of 0.8 mm, and a length of 20 cm.

FIG. 2 shows a wedge-shaped vertical section of a gel membrane having a minimum thickness (at a start point in the direction of electrophoresis) of 0.8 mm, linearly increasing to a maximum thickness (at an end point in the direction of electrophoresis) of 1.6 mm, and a length of 20 cm.

FIG. 3 shows a wedge-shaped vertical section of a gel membrane having a minimum thickness (at a start point in the direction of electrophoresis) of 0.8 mm, exponentially increasing to a maximum thickness (at an end point in the direction of electrophoresis) of 1.6 mm, and a length of 20 cm.

FIG. 4 shows a V-shaped vertical section of a gel membrane having a maximum thickness (at a start point and an end point in the direction of electrophoresis) of 300 $\mu$m, a minimum thickness (at the center in the direction of electrophoresis) of 150 $\mu$m, and a length of 40 cm.

FIG. 5 shows a wedge-shaped vertical section of a gel membrane having a minimum thickness (at a start point in the direction of electrophoresis) of 150 $\mu$m, linearly increasing to a maximum thickness (at an end point in the direction of electrophoresis) of 300 $\mu$m, and a length of 40 cm.

FIG. 6 shows a wedge-shaped vertical section of a gel membrane having a minimum thickness (at a start point in the direction of electrophoresis) of 150 μm, exponentially increasing to a maximum thickness (at an end point in the direction of electrophoresis) of 300 μm, and a length of 40 cm.

DETAILED DESCRIPTION OF THE INVENTION

Figure 1:
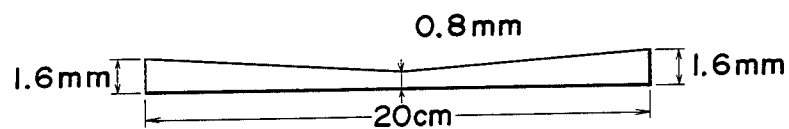
FIGS. 1 to 6 are vertical sectional views showing representative thickness gradients of the gel membrane (gradient in the direction of electrophoresis) according to the present invention.

Examples of the acrylamide compound employable in the present invention include acrylamide and its homologues such as N-methylacrylamide, N,N-dimethylacrylamide, N-(hydroxymethyl)acrylamide and diacetoneacrylamide, as well as methacrylamide and its homologues. These compounds can be employed independently or in combination. Acrylamide is most preferred among these acrylamide compounds, and this acrylamide can be also preferably employed in combination with one or more of other acrylamide compounds.

As the crosslinking agent employable to obtain the polyacrylamide gel membrane, a known crosslinking agent described, for instance, in "Electrophoresis" 1981, 2, 213–228 can be employed single or in combination. Examples of the crosslinking agents include bifunctional compounds such as N,N-methylenebisacrylamide (BIS), N,N'-propylenebisacrylamide (PBA), di(acrylamide dimethyl)-ether (i.e., N,N'-oxydimethyleneacrylamide), 1,2-diacrylamide ethyleneglycol (DEG), 1,3-diacryloylethyleneurea (EUB), ethylene diacrylate (EDA), N,N'-diallyltartardiamide (DATD), and N,N'-bisacrylylcystamine (BAC). Examples of the crosslinking agents also include trifunctional compounds such as 1,3,5-triacryloylhexahydro-s-triazin, triallylcyanurate, and triallylisocyanurate.

The crosslinking agent can be employed in an amount of approx. 1 to 30 wt. %, preferably approx. 2 to 10 wt. %, based on the total weight of the monomer (i.e., acrylamide compound) and the crosslinking agent.

The gel membrane preferably contains agarose. There is no specific limitation on the agarose to be contained in the gel membrane, and any type of agarose such as low-electroendosmosis agarose, medium-electroendosmosis agarose, or high-electroendosmosis agarose can be employed. Examples of agarose employable in the invention include agaroses disclosed in U.S. Pat. No. 4,290,911, GB 2 042 571A, WO 82/02599, U.S. Pat. No. 4,319,976, etc. The amount of agarose to be added ranges from approx. 0.2 to 2.0 wt(g)/v(ml) %, preferably from approx. 0.3 to 1.2 wt(g)/v(ml) %, based on the volume of the aqueous gel containing the monomer and the crosslinking agent.

The gel membrane of the invention may contain a water-soluble polymer. As the water-soluble polymer, a water-soluble polymer of the addition polymerization type or condensation polymerization type, a crosslinked acrylamide copolymer containing a vinylsulfonyl group, or a water-soluble cellulose derivative can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. Examples of the closs-linked acrylamide copolymers include N-[[3-(2-vinylsulfonyl)-propaneamide]methyl]acylamideacrylamide copolymer, N-[[3-(2-chloroethylsulfonyl)propaneamide]methyl]acrylamide-acrylamide-N-(1,1-dimethyl-3-oxobutyl)acrylamide copolymer. Examples of the water-soluble cellulose derivatives include water-soluble cellulose ether such as methyl cellulose, ethyl cellulose, hydoxy ethyl cellulose, hydroxypropyl methyl cellulose, hydroxybutyl methyl cellulose. Among these water-soluble polymers, polyacrylamide, polyethylene glycol, N-[[3-(vinylsulfonyl)propaneamide]methyl]acrylamide-acrylamide copolymer are preferred. The water-soluble polymer is used in a range of approx. 2 to 100 wt. %, preferably, approx. 5 to 50 wt. %, based on the total weight of the monomer and the crosslinking agent, in the case that the water-soluble anionic polymer of the addition polymerization type or condensation polymerization type is used. In the case that the closslinked acrylamide copolymer is used, the water-soluble polymer can be used in a range of approx. 1 to 50 wt. %, preferably, approx. 5 wt. % to 40 wt. %, based on the weight of the acrylamide compound.

Glycerol can be contained in the gel membrane to prevent prolongation and distortion of the bands so as to read the resolved pattern. The glycerol can be introduced in an amount of approx. 0.1 to 1.0 wt(g)/v/(ml) % based on the volume of the gel membrane.

A polyol compound such as glycerol or ethylene glycol can be contained in the aqueous gel membrane of the means of the invention as a wetting agent. The polyol compound can be introduced in an amount of approx. 5 to 40 wt(g)/v(ml) % based on the volume of the gel membrane.

The agarose and/or the water-soluble polymer or the polyol compound can be added to the gel membrane at a stage when the acrylamide compound and the closslinking agent are dissolved in water until at a stage when the aqueous polyacrylamide gel is formed.

The means for electrophoresis of the invention can be employed for analysis of proteins and conjugated proteins (e.g., lipoproteins, glycoproteins, etc.) and the electrophoresis layer (gel membrane) of the means may comprise an anionic surfactant as a modifier. The use of the anionic surfactant is generally essential or preferable for the electrophoretic analyses of proteins or conjugated proteins, because it contributes to perform separation of the protein and conjugated protein and determination of molecular weight of these proteins. However, the electrophoresis layer may not contain the anionic surfactant.

Examples of the anionic surfactant include alkylsulfates, particularly alkylsulfates having a long chain alkyl group of at least 10 carbon atoms. The cation contained for formation of the salt generally is an alkali metal ion such as sodium ion, potassium ion, or lithium ion. Sodium ion is preferred from the economical viewpoint. The alkylsulfates preferably are dodecylsulfates (salts of sodium, potassium, lithium, etc.), and particularly preferred is sodium dodecylsulfate (SDS). The introduction of SDS into the gel membrane is particularly advantageous for separation of proteins and conjugated proteins, as well as for determination of their molecular weights. The anionic surfactant (modifier) can be contained in the gel-forming solution in an amount of not more than about 2.0 wt(g)/v(ml) % (weight per volume of the gel-forming solution), preferably approx. 0.1 to 1.5 wt(g)/v(ml) %. The anionic surfactant can be added at a stage when the acrylamide and the closslinking agent are dissolved in water until at a stage when the aqueous polyacrylamide gel is formed.

Various surfactants such as a nonionic surfactant, an anionic surfactant or an amphoteric surfactant differing from the modifier can be added to the gel medium. Examples of such surfactants are described hereinbelow.

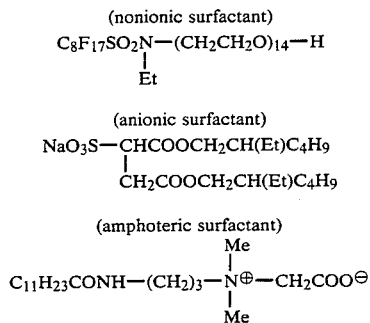

In the above formulae, Et means ethyl and Me means methyl.

The amount of the nonionic surfactant or cationic surfactant is in the range of approx. $1 \times 10^{-4}$ to $5 \times 10^{-1}$ wt(g)/v(ml) %, preferably approx. $1 \times 10^{-3}$ to $1 \times 10hu -2$ wt(g)/v(ml) % based on the volume of the aqueous gel membrane containing the monomer and the crosslinking agent. The amount of the anionic surfactant is in the range of approx. $1 \times 10^{-4}$ to $5 \times 10^{-2}$ wt(g)/v(ml) %, preferably approx. $1 \times 10^{-3}$ to $5 \times 10^{-2}$ wt(g)/v(ml) %.

The means for electrophoresis of the invention also can be employed for determination of base sequence of DNA, RNA, their fragments, and their derivatives. For this purpose, a compound containing at least one carbamoyl group is generally incorporated into the gel membrane medium as a modifier. Examples of the modifiers includes urea and formamide. Urea is most preferred. The modifier can be used in an amount of approx. 40 to 60 wt. % based on the volume of the aqueous gel membrane containing the monomer and the crosslinking agent. In the case that urea is used as a modifier, the amount generally ranges from approx. 6 moles (approx. 360 g.) per one liter of the aqueous gel containing the monomer and the crosslinking agent to the saturation amount, preferably from about 7 moles (approx. 420 g.) to the saturation amount.

In the gel membrane for electrophoresis of protein and protein derivatives, a buffer agent which is able to buffer a solution to a range of pH 2.5 to 10.0 can be incorporated. Such buffer agent are described in publications such as "Chemistry Handbook, Fundamental Edition" compiled by The Chemical Society of Japan (Maruzen Ltd., Tokyo, 1966) pp. 1312-1320; "Modern Electrophoresis" edited by Aoki and Nagai (Hirokawa Shoten, 1973), pp. 320-322; "Data for Biochemical Research" compiled by R.M.C. Dawson et al., second edition (Oxford at the Clarendon Press, 1969) pp. 476-508; "Biochemistry" 5, 467 (1966); and "Analytical Biochemistry" 104, pp. 300-310 (1966). Examples of the buffer agents include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)-glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-[tris(hydroxymethyl)methyl]-3-aminopropanesulfonic acid (TAPS) or its salt. Preferable examples of the buffer agents include potassium dihydrogenphosphate-disodium hydrogenphosphate, Tris-sodium borate, Tris-sodium borate-EDTA·2Na, Tris-citric acid, sodium barbital-sodium acetate, sodium barbital-hydrochloric acid, barbitol-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, and sodium salt of TAPS.

In the gel membrane for electrophoresis of DNA and the like, a buffer agent which is able to buffer a solution to a range of pH 8.0 to 10.0, preferably pH 8.0 to 9.0 can be incorporated. Such buffer agents are also described in the aforementioned publications.

Examples of the buffer agents include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroymethy)-methyl]-3-aminopropanesulfonic acid (TAPS) or its Na or K salt; as well as an acid, an alkali, and a salt employable in combination with the compounds. Preferably examples of the buffer agents include a combination of Tris and boric acid-EDTA·2Na (pH 8.2 to 8.3), and a combination of Tris and hydrochloric acid (pH 8.9).

The gel membrane preferably is colorless and transparent for readily detecting or reading the obtained electrophoretic patterns.

The gel membrane can be prepared as a layer, a membrane or a slab having a predetermined and controlled thickness gradient on a sheet-type (or film-type, or plate-type) support or covering sheet which has a nonconductive and water impermeable smooth surface. An organic polymer sheet or a glass plate can be employed as the support or covering sheet. The organic polymer sheet means a polymer material in the form of a sheet (or plate). Examples of the organic polymer include polyethylene terephthalate, polycarbonate of Bisphenol A, polstyrene, cellulose ester such as cellulose diacetate, cellulose triacetate, cellulose acetate propionate, or the like. The organic polymer sheet has a thickness in the range of approx. 50 μm to 2 mm, preferably approx. 80 μm to 500 μm. The organic polymer sheet is transparent and has a smooth surface through which an electromagnetic rays having at least a part of the range of wavelength in the range of approx. 200 to 900 nm can be penetrate.

The surface of the organic polymer support or covering sheet employed in the invention can be made hydrophilic to improve adhesion. Known methods for making a surface of a polymer material hydrophilic such as irradiation of ultraviolet rays, glow discharge treatment, corona discharge treatment, flame treatment, irradiation of electron radiation of chemical etching can be used. If desired, in order to improve the adhesion between the gel membrane and the support (or the covering sheet), a undercoating layer or an adhesive layer can be provided on a surface of the organic polymer support or covering sheet. A plane support or covering sheet which has a predetermined gradual thickness variation (described hereinafter) can be used.

The gel membrane of the means of the invention can be prepared by a process in which an aqueous solution containing the above-described components and a radical polymerization initiator (gel-forming solution) is coated or casted by a known method on a plane support or covering sheet having a smooth surface. The gel forming solution is then crosslinked to undergo polymerization on the surface of the support or covering sheet. The crosslinking polymerization can be initiated by a known method, for instance, in the presence of a peroxide and/or under irradiation of ultraviolet rays. The reaction can be accelerated by heat and irradiation with ultraviolet rays.

An acrylamide compound and a crosslinking agent are dissolved or dispersed in water to prepare an aqueous solution or an aqueous dispersion, wherein the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

As the polymerization catalyst, a known low temperature-polymerization initiator such as those described in "Electrophoresis" 1981, 2, 213-219, ibid. 1981, 2, 220-228; and "Modern Electrophoresis" edited by Aoki & Nagai (Hirokawa Shoten, 1973) can be used. Examples of the initiators include a mixture of $\beta$-dimethylaminopropionitrile (DMAPN) and ammonium peroxodisulfate, a mixture of N,N,N',N'-tetramethylethylenediamine (TEMED) and ammonium peroxodisulfate, a mixture of TEMED and riboflavin (riboflavin phosphate sodium salt), a combination of a mixture of TEMED, riboflavin and hydrogen peroxide, and irradiation with ultraviolet rays. The radical reaction initiator can be employed in the amount of approx. 0.3 to 5 wt. %, preferably approx. 0.5 to 3 wt. %, based on the total amount of the monomer and crosslinking agent.

The gel concentration preferably is in the range of approx. 3 to 30 wt(g)/v(ml) % (total weight of the monomer and crosslinking agent per total volume of gel membrane comprising a monomer, a crosslinking agent and an aqueous medium), the concentration being expressed in accordance with the definition indicated by S. Hjerten in Arch. Biochem. Biophys. 1 (Suppl.) 147 (1962).

In the case that the gel forming solution is crosslinked on the surface of the plastic film serving as a covering film, the surface of the gel forming solution layer can be covered with a plastic film (including sheet and plate, which serves as a support). As the covering material, materials same as the above-described plane-type support can be used. In the case that the covering film is an organic polymer film, the thickness is not larger than approx. 300 $\mu$m, for practical use in the range of approx. 4 to 250 $\mu$m, preferably in the range of approx. 50 to 200 $\mu$m. In the case that the covering materials is a glass plate, the thickness is same as a plane glass plate employed as the support.

The gel membrane generally has a thickness gradient wherein the side for a low molecular weight portion is made larger than the side for a high molecular weight portion. The gel membrane having other thickness gradient may also be used. The thickness gradient (curve or straight line) of the gel membrane may be a straight line, a slightly bended straight line, a part of gradual variation curve such as an exponential function, a logarithmic function, a suspension line, a tracking line, a parabola, a hyperbola, an ellipsoidal line and tertiary curve, and a combination thereof or a combination of curve with a straight line. The thickness gradient preferably increases from one end to another end gradually and monotonously in the direction of electrophoresis, or increases from an intermediate position to one end in the direction of electrophoresis, or increases after initially decreasing the thickness. The range of the thickness variation is from approx. 50 $\mu$m to 5mm, preferably approx. 80 $\mu$m to 2 mm. In the gel membrane of the means of electrophoresis of DNA and the like, the range of thickness variation preferably is approx. 300 $\mu$m to 3 mm. The start point may have an optional shape selected from the known forms such as a rectangle, a square, a triangle (shark's teeth type) and a circle.

Preferably, the gel membrane of the invention has one of the following characteristics:

the thickness gradient of the membrane is formed under the condition that at least one end of the membrane is the thickest;

the thickness gradient of the membrane is formed under the condition that one end of the membrane is the thickest and another end of the membrane is the thinnest;

the thickness gradient of the membrane is formed under the condition that the thinnest portion lies between positions at 10% (preferably 20%, more preferably 30%) of the length of the membrane in the electrophoresis direction apart inside from both ends of the membrane;

the thickness gradient of the membrane is formed under the condition that thickness of the thinnest portion is less than 80% (preferably less than 70%, more preferably less than 60%) of thickness of the thickest portion; and the thickness gradient of the membrane is formed under the condition that thickness of the thinnest portion is more than 20% (preferably more than 30%, more preferably more than 40%) of thickness of the thickest portion.

The gel membrane having a thickness gradient can be prepared by the following processes:

(1) the gel-forming solution is introduced into a mold covered with sheet-type covering material which is formed by placing a spacer plate having a thickness gradient (layer thickness gradient or membrane thickness gradient) on a surface of a plane support and then cross-linking polymerized;

(2) the gel-forming solution is introduced into a mold covered with the covering material (support) which is formed by placing a spacer plate having a uniform thickness on a surface of a plane support (or covering sheet) having a thickness gradient corresponding to the predetermined gradual thickness variation and then cross-linking polymerized;

(3) the gel-forming solution is casted on a surface of a plane support (or covering sheet) having a thickness gradient corresponding to the predetermined thickness gradient and then crosslinking polymerized under oxygen-free condition, such as nitrogen gas atmosphere; and free condition, such as nitrogen gas atmosphere; and (4) the gel-forming solution is coated and casted by controlling the flow rate per unit time corresponding to the predetermined thickness gradient (the flow rate is reduced in the thinnest area (area to have the smallest thickness), while the flow rate is increased in the thickest area) on a plane support (or covering sheet) and then crosslinking polymerized under oxygen-free condition such as a nitrogen gas atmosphere.

The plane support having a predetermined thickness gradient can be prepared by various known manners such as a mold-casting method, a chemical etching and a cutting method. In the case that the gel-forming solution is coated and casted on the support (or covering sheet) while controlling the flow rate, the spacer is not necessary to have a thickness gradient corresponding to the predetermined thickness gradient of the gel membrane.

In the gel membrane, the thickness gradient can be given in the area being a little wider than the migration area, and the thickness of the residual area is made uniform. The gel membrane having such thickness gradient utilized for an embodiment employing a plane support or covering sheet having a gradual thickness variation.

The gel membrane of the invention can be prepared essentially in the same manner as for the preparation of the known aqueous polyacrylamide gel membrane. The gel membrane of the invention can be horizontally or vertically placed for performing slab gel electrophoresis in the known manners.

The present invention will be described in more detail hereinbelow with reference to the following examples without limiting the invention.

EXAMPLE 1 AND COMPARISON EXAMPLE 1

Figure 2:
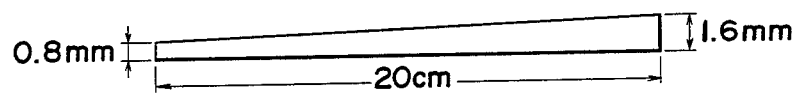
Figure 3:
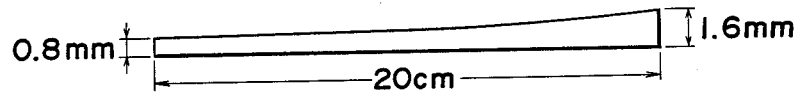

A surface of square, colorless, transparent sheet of polyethylene terephthalate (PET) (width: 20 cm, length: 20 cm, thickness: 180 μm) was treated with irradiation of ultraviolet rays. The PET film was itself used as a support. On both sides of the PET film were fixed spacer plates having a width of 10 mm and a thickness gradient given respectively in the sectional views of FIGS. 1 to 3, and a spacer plate having a width of 10 mm and a uniform thickness of 0.8 mm. The fixed spacer plates were covered with the PET sheet (covering sheet, thickness: 100 μm), and then outside of the covering sheet was fixed using a square aluminum plate (size: 20 cm × 20 cm) corresponding to the thickness gradient of the spacer plates to obtain a mold for the preparation of a gel membrane for electrophoresis composed of an aqueous polyacrylamide gel.

Into the mold was introduced the gel-forming solution having a composition given in Table 1, and then was left for 10 minutes. The gel-forming solution was subjected to crosslinking polymerization between two PET sheets (support and covering sheet) by irradiating 100 W of high pressure mercury lamp placed at a distance of 10 cm at a temperature of 25° C. Thus, the aqueous polyacrylamide gel membranes (1), (2) and (3) having a thickness gradient, and an aqueous polyacrylamide gel membrane (a) (for comparison) having a uniform thickness of 0.8 mm were obtained.

Electrophoresis of the following human serum proteins were performed in the conventional manner using the gel membranes (1), (2), (3) & (a).

Standard protein (human albumin, molecular weight: 67,000)

Lactate dehydrogenase, sub unit (molecular weight: 36,000)

Catalase, sub unit (molecular weight: 60,000)

Ferritine, sub unit (molecular weight: 18,500)

Ferritine, half unit (molecular weight: 220,000)

Tyroglobulin, sub unit (molecular weight: 330,000)

The samples were then dyed by Coomassie Blue R-250 (Colour Index Constitution Number 42660).

The range of the molecular weight using the gradient gel membranes (1), (2), (3) which can be segregated and fractionated was from 10,000 to 330,000 or more. The range of the molecular weight using the gradient gel membrane (a) which can be segregated and fractionated was from 10,000 to between 200,000 and 330,000.

Thus, it was confirmed that the aqueous polyacrylamide gel membrane of the present invention had an improved molecular sieve function in the wide range from a low molecular weight portion to a high molecular weight portion.

TABLE 1

| Composition of Gel-forming Solution | |
|---|---|
| Acrylamide | 11.9 g |
| N,N'—methylenebisacrylamide | 600 mg |
| Sodium dodecylsulfate | 100 mg |
| 1,5M Tris-sodium chloride (buffer agent) (adding water to 100 ml) | 25 ml |
| Peroxoammonium disulfate (polymerization initiator, 2.5 wt. % aqueous solution) | 2.4 ml |
| N,N,N',N'—tetramethylethylene diamine (polymerization initiator, 25 wt. % aqueous solution) | 25 μl |
| Sodium salt of riboflavin phosphate (polymerization initiator, 25 wt. % aqueous solution) | 2.0 ml |

Remark Tris: tris(hydroxymethyl)aminomethane

EXAMPLE 2 AND COMPARISON EXAMPLE 2

A polyacrylamide gel membrane (b) having a gel concentration gradient was prepared using the same mold having a uniform thickness 0.8 mm as in Comparison Example 1, and then the composition of the gel-forming solution was introduced into the mold while the mixture proportion of the gel-forming solution was gradually changed as shown in Table 2.

The gel membrane (2) prepared in Example 1 and the gel membrane (b) were dyed by Coomassie Blue R-250.

The gel membrane (2) was not distorted in the dyeing process and the swelling proportion was constant.

The gel membrane (b) having a gel concentration gradient was distorted as a whole, slightly distorted in a low gel concentration portion, highly distorted in a high gel concentration portion.

In the thickness gradient gel membrane of the invention, the distortion was not observed in the dyeing process.

TABLE 2

| Composition of Gel-forming Solution | A | B |
|---|---|---|
| Acrylamide | 5.7 g | 19.0 g |
| N,N'—methylenebisacrylamide | 300 mg | 1.0 g |
| Sodium dodecylsulfate | 100 mg | 100 mg |
| 1,5M Tris-sodium chloride (buffer agent) (adding water to 100 ml) | 25 ml | 25 ml |
| Peroxoammonium disulfate (polymerization initiator, 2.5 wt. % aqueous solution) | 2.4 ml | 2.4 ml |

TABLE 2-continued

| Composition of Gel-forming Solution | A | B |
|---|---|---|
| N,N,N',N'—tetramethylethylene diamine (polymerization initiator, 25 wt. % aqueous solution) | 25 ml | 25 µl |
| Sodium salt of riboflavin phosphate (polymerization initiator, 25 wt. % aqueous solution) | 2.0 ml | 2.0 ml |

Remark Tris: tris(hydroxymethyl)aminomethane

EXAMPLE 3 AND COMPARISON EXAMPLE 3

A surface of square, colorless, transparent PET film (width: 20 cm, length: 20 cm, thickness: 180 µm) was treated with irradiation of ultraviolet rays. The PET film was itself used as a support. On both sides of the PET film was fixed a spacer plate having a uniform thickness of 0.8 mm, a width of 10 mm and a length 20 cm.

On the support was casted and coated the gel-forming solution having a composition given in Table 1 to give a layer thickness in the range of 0.8 mm to 1.6 mm by controlling the flow rate and the coated layer was subjected to crosslinking polymerization by irradiating 500 W of xenon lamp in a nitrogen atmosphere. The gel membrane was covered with the PET sheet (thickness : 63 µm, size: 20×20 cm) and was then bound to obtain aqueous polyacrylamide gel membranes having same thickness gradient of the gel membranes (1), (2) and (3).

A gel membrane (c) having a uniform thickness of 0.8 mm was prepared in the same manner as mentioned above, except that the flow rate of the gel forming solution was controlled to give a thickness of 0.8 mm.

Electrophoresis of the samples were performed using the above obtained four gel membranes in the same manner as in Example 1 and Comparison Example 1. Almost the same results were obtained.

EXAMPLE 4 AND COMPARISON EXAMPLE 4

Figure 4:
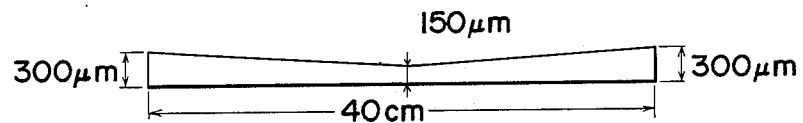
Figure 5:
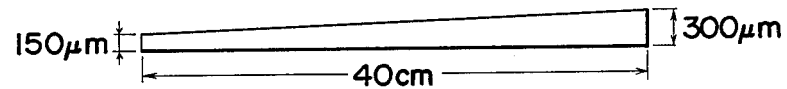
Figure 6:
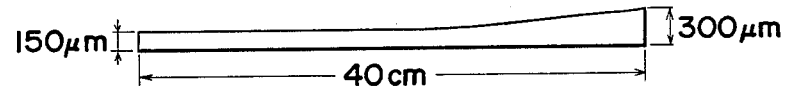

A surface of rectangular, colorless, transparent PET film (width: 20 cm, length: 40 cm, thickness: 180 µm) was treated with irradiation of ultraviolet rays. The PET film was itself used as a support. On both lateral sides of the PET film were fixed spacer plates having a width of 10 mm and a thickness gradient given respectively in the sectional views of FIGS. 4 to 6, and a spacer plate having a width of 10 mm and a uniform thickness of 200 µm. The fixed spacer plates were covered with the PET sheet (covering sheet, thickness: 100 µm), and then the outer side of the covering sheet was fixed using a square aluminum plate (size: 20 cm×40 cm) corresponding to the thickness gradient of the spacer plates to obtain a mold for the preparation of a gel membrane for electrophoresis composed of an aqueous polyacrylamide gel.

Into the molds was introduced the gel-forming solution having a composition given in Table 3, and then was left for 10 minutes. The gel-forming solution was subjected to crosslinking polymerization between two PET sheets by irradiating 100 W of high pressure mercury lamp at a temperature of 25° C. Thus, aqueous polyacrylamide gel membrane (4), (5) and (6) having a thickness gradient, and a polyacrylamide gel membrane (d) having a uniform thickness of 100 µm.

Evaluations of the gel membrane (4), (5), (6) & (d) were made on the determination of base seqauence of DNA in the conventional manner using a sample prepared by a dideoxy method for M13-mp8 DNA. The readable range of the resolved fragments is shown below:

gel membrane (4): fragments from No. 60 to No. 240
gel membrane (5): fragments from No. 60 to No. 215
gel membrane (6): fragments from No. 60 to No. 240

The widths and spaces of the resolved fragments on each lane not so narrow as to disturb the desired analysis.

The readable range of the resolved fragments on the gradient gel membranes (d) was No. 60 to No. 200 (namely, 60th to 200th), and the width and space of the resolved fragments gradually narrowed from the low molecular weight portion to the high molecular weight portion.

Thus, it was confirmed that the aqueous polyacrylamide gel membrane of the invention had an improved molecular sieve function in the wide range from a low molecular weight portion to a high molecular weight portion. Further, the gel membrane of the invention showed an improved resolving power for the determination of base sequence of DNA.

TABLE 3

| Composition of Gel-forming Solution | |
|---|---|
| Acylamide | 7.66 g |
| 1,3,5-Triacryloyl-hexahydro-s-triazine | 340 mg |
| Agarose | 450 mg |
| Urea | 42.0 g |
| Tris (buffer agent) | 1.21 g |
| Borate (buffer agent) | 650 mg |
| EDTA.2Na (buffer agent) (addition of water to 100 ml) | 75 mg |
| Peroxo ammonium disulfate (polymerization initiator, 5 wt. % aqueous solution) | 1.3 ml |
| N,N,N',N'—tetramethylethylene diamine (polymerization initiator, 25 wt. % aqueous solution) | 33 µl |
| Sodium salt of riboflavin phosphate (polymerization initiator, 25 wt. % aqueous solution) | 2.0 ml |

Remark Agarose: low electric permeability, gelling point; 36° C.
Tris: tris(hydroxymethyl)aminomethane

EXAMPLE 5 AND COMPARISON EXAMPLE 5

A surface of rectangular, colorless, transparent PET sheet (thickness: 180 µm, size: 20 cm×40 cm) was treated with irradiation of ultraviolet rays. The PET film was itself used as a support. One both lateral sides of the PET film were fixed spacer plates having a width of 10 mm, a length of 40 cm and a uniform thickness of 300 µm.

On the support was casted and coated the gel-forming solution having a composition given in Table 3 to give a layer thickness in the range of 150 µm to 300 µm by controlling the flaw rate, and the coated layer was subjected to crosslinking polymerization by irradiating 500 W of xenon lamp in a nitrogen atmosphere. The gel membrane was covered with the PET sheet (thickness : 63 µm, size: 20×40 cm) and was bound to obtain aqueous polyacrylamide gel membranes having a same thickness gradient of the gel membranes (4), (5) and (6).

A gel membrane (e) for comparison having a uniform thickness of 200 µm was prepared in the same manner as mentioned above, except that the flow rate of the gel forming solution was controlled to give a thickness of 200 µm.

Electrophoresis was performed using the above obtained gel membranes in the same manner as in Example 4 & Comparison Example 4. Almost the same results were obtained.

EXAMPLE 6 AND COMPARISON EXAMPLE 6

A surface of rectangular, colorless, transparent PET sheet (thickness: 180 μm, size: 20 cm×40 cm) was treated with irradiation of ultraviolet rays. The PET film was itself used as a support. On both lateral sides of the PET film were fixed spacer plates having a width of 10 mm, a length of 40 cm and a uniform thickness of 200 μm.

Figure 7:
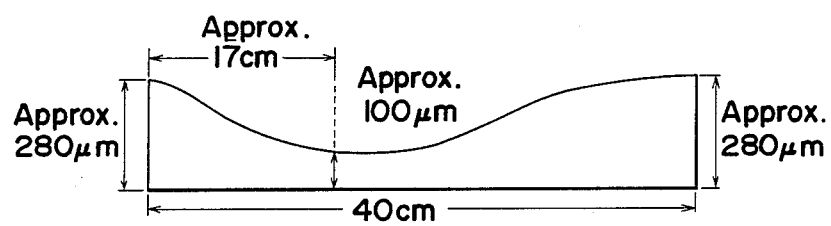
FIG. 7 shows a vertical section of a gel membrane having a hyperbola line continuing to shallow suspension line, a minimum thickness (at the center which is 18 cm apart inside from the start point in the direction of electrophoresis) of 100 μm, a maximum thickness (at a start point and an end point in the direction of electrophoresis), and a length of 40 cm.

On the support was casted and coated the gel-forming solution having a composition given in Table 3 to give a layer thickness in the range of 100 μm to 280 μm by controlling the flow rate, and the coated layer was subjected to crosslinking polymerization by irradiating 500 W of xenon lamp in a nitrogen atmosphere. The gel membrane was covered with the PET sheet (thickness : 63 μm, size: 20×40 cm) and was bound to obtain aqueous polyacrylamide gel membrane (7) having a thickness gradient shown in FIG. 7.

A gel membrane (f) for comparison having a uniform thickness of 200 μm was prepared in the same manner as mentioned above, except that the flow rate of the gel forming solution was controlled to give a thickness of 200 μm.

Evaluation of two gel membranes (7) and (f) was made on the determination of base seqauence of DNA in the same manner as in Example 4. The readable range of resolved fragments of the gel membrane (7) of the present invention was from No. 60 to No. 200, and the width and space of the resolved fragments in each lane were not so narrow as to disturb the desired analysis of the resolved fragments.

The readable range of the resolved fragments on the gradient gel membrane (f) for comparison was from No. 60 to No. 200, and the width and space of the resolved fragments gradually narrowed from the low molecular weight portion to the high molecular weight portion.

We claim:

1. A means for electrophoresis comprising a membrane of an aqueous polyacrylamide gel formed by crosslinking polymerization of an acrylamide compound and a crosslinking agent in the presence of water sandwiched between a support and a covering sheet, wherein said membrane has a thickness gradient in its electrophoresis direction such that the thinnest portion lies in an area which is at least 10% of the length of the membrane in the electrophoresis direction from both ends of the membrane.

2. The means for electrophoresis as claimed in claim 1 wherein said thickness gradient of the membrane is such that the thinnest portion lines in an area which is at least 20% of the length of the membrane in the electrophoresis direction from both ends of the membrane.

3. The means for electrophoresis as claimed in claim 1, wherein said thickness gradient of the membrane is formed under the condition that thickness of the thinnest portion is less than 80% of thickness of the thickest portion.

4. The means for electrophoresis as claimed in claim 1, wherein said thickness gradient of the membrane is formed under the condition that thickness of the thinnest portion is more than 20% of the thickness of the thickest portion.

5. The means for electrophoresis as claimed in claim 1, wherein said membrane contains a compound at least one carbamoyl group as a modifier.

6. The means for electrophoresis as claimed in claim 1, wherein said membrane contains an anionic surfactant as a modifier.

7. The means for electrophoresis as claimed in claim 1, wherein said membrane contains a water soluble polymer.

8. The means for electrophoresis as claimed in claim 8, wherein said membrane contains agarose.

* * * * *